United States Patent
Goldberg et al.

(10) Patent No.: US 6,203,989 B1
(45) Date of Patent: Mar. 20, 2001

(54) METHODS AND COMPOSITIONS FOR AMPLIFYING DETECTABLE SIGNALS IN SPECIFIC BINDING ASSAYS

(75) Inventors: Martin J. Goldberg, Saratoga; Govinda Rao S. Yelagalawadi, San Jose; Eugene Yuji Tanimoto, Menlo Park; Huu Minh Tran, Milpitas; Helin Dong, Palo Alto; David Lockhart, Mountain View; Thomas B. Ryder, Los Gatos; Janet A. Warrington, Los Altos; Jody Beecher, San Jose, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/276,774

(22) Filed: Mar. 25, 1999

Related U.S. Application Data (60) Provisional application No. 60/102,577, filed on Sep. 30, 1998.

(51) Int. Cl.[7] .................................................. C12Q 1/68
(52) U.S. Cl. .................. 435/6; 435/287.2; 435/287.3; 435/7.1; 436/501; 436/514; 436/807; 536/23.1; 536/24.1
(58) Field of Search .............................. 435/6, 7.1, 237.2, 435/237.3, 91; 436/501, 514, 807; 536/23.1, 24.3, 25.3, 27; 356/344; 422/50, 63, 68.1, 69, 98, 99

(56) References Cited

U.S. PATENT DOCUMENTS 4,711,955   12/1987   Ward et al. .

(List continued on next page.)

FOREIGN PATENT DOCUMENTS

0154884 A2   9/1985   (EP) .

(List continued on next page.)

OTHER PUBLICATIONS

Kerstens, H. et al. (1995). "A Novel in Situ Hybridation Signal Amplification Method Based on the Deposition of Biotinylated Tyramine" *J. Histochemistry and Cytochemistry* 43(4):347–352.

(List continued on next page.)

*Primary Examiner*—W. Gary Jones
*Assistant Examiner*—Janell E. Taylor
(74) *Attorney, Agent, or Firm*—Philip L. McGarrigle (57) ABSTRACT

Methods and compounds are provided for detecting target molecules in a sample using specific binding assays. In particular, methods are provided for detecting a nucleic acid target in a sample. In one embodiment, the method comprises hybridizing a nucleic acid target, comprising a target nucleic acid sequence, to a nucleic acid probe, comprising a probe nucleic acid sequence, wherein the target comprises a binding ligand. The hydridized target is contacted with a receptor comprising multiple sites capable of binding the binding ligand to complex the receptor to the binding ligand, and the receptor is contacted with an amplification reagent, comprising a plurality of the binding ligands, to complex the amplification reagent to the receptor. The presence of the complexed amplification reagent then is detected, for example, by detecting the presence of a detectable label, such as a fluorescent label, for example, on the receptor or the amplification reagent. Optionally, the amplification reagent, comprising a plurality of the binding ligands, is contacted with labeled receptor molecules thereby to complex a plurality of labeled receptor molecules to the amplification reagent, and the labeled receptor molecules complexed to the amplification reagent are detected. This permits the detectable signal to be enhanced and amplified. In one embodiment, the binding ligand is biotin, the receptor is streptavidin, and the amplification reagent is an antibody or a DNA matrix. In another embodiment, an array of different nucleic acid probes immobilized on a surface, each having a defined sequence and location on the surface, may be used in the assays, thus permitting screening and detection of binding of a large number of nucleic acids.

35 Claims, 1 Drawing Sheet

U.S. PATENT DOCUMENTS

| | | |
|---|---|---|
| 4,882,269 | 11/1989 | Schneider et al. . |
| 4,910,300 | 3/1990 | Urdea et al. . |
| 5,124,246 | 6/1992 | Urdea et al. . |
| 5,143,854 | 9/1992 | Pirrung et al. . |
| 5,175,270 * | 12/1992 | Nilsen et al. .................... 536/27 |
| 5,252,743 | 10/1993 | Barrett et al. . |
| 5,310,523 | 5/1994 | Smethers et al. . |
| 5,359,100 | 10/1994 | Urdea et al. . |
| 5,384,261 | 1/1995 | Winkler et al. . |
| 5,412,087 | 5/1995 | McGall et al. . |
| 5,424,186 | 6/1995 | Fodor et al. . |
| 5,451,683 | 9/1995 | Barrett et al. . |
| 5,484,904 | 1/1996 | Nilsen et al. . |
| 5,487,973 | 1/1996 | Nilsen et al. . |
| 5,510,270 | 4/1996 | Fodor et al. . |
| 5,512,436 * | 4/1996 | Stone .................................. 435/6 |
| 5,527,681 | 6/1996 | Holmes . |
| 5,545,531 | 8/1996 | Rava et al. . |
| 5,547,839 | 8/1996 | Dower et al. . |
| 5,552,280 | 9/1996 | Urdea et al. . |
| 5,561,043 | 10/1996 | Cantor et al. . |
| 5,571,639 | 11/1996 | Hubbell et al. . |
| 5,571,670 | 11/1996 | Urdea . |
| 5,578,832 | 11/1996 | Trulson et al. . |
| 5,580,731 | 12/1996 | Chang et al. . |
| 5,591,584 | 1/1997 | Chang et al. . |
| 5,594,117 | 1/1997 | Urdea et al. . |
| 5,594,118 | 1/1997 | Urdea et al. . |
| 5,597,909 | 1/1997 | Urdea et al. . |
| 5,599,695 | 2/1997 | Pease et al. . |
| 5,614,362 | 3/1997 | Urdea . |
| 5,624,711 | 4/1997 | Sundberg et al. . |
| 5,624,802 | 4/1997 | Urdea et al. . |
| 5,629,153 | 5/1997 | Urdea . |
| 5,631,734 | 5/1997 | Stern et al. . |
| 5,635,352 | 6/1997 | Urdea et al. . |
| 5,656,731 | 8/1997 | Urdea . |
| 5,677,195 | 10/1997 | Winkler et al. . |
| 5,702,893 | 12/1997 | Urdea et al. . |
| 5,710,000 | 1/1998 | Sapolsky et al. . |
| 5,710,264 | 1/1998 | Urdea et al. . |
| 5,736,316 | 4/1998 | Irvine et al. . |
| 5,744,305 | 4/1998 | Fodor et al. . |
| 5,804,384 * | 9/1998 | Muller et al. .................... 435/6 |

FOREIGN PATENT DOCUMENTS

| | | |
|---|---|---|
| WO 89/03891 | 5/1989 | (WO) . |
| WO 90/04786 | 5/1990 | (WO) . |
| WO 92/10092 | 6/1992 | (WO) . |
| WO 93/09668 | 5/1993 | (WO) . |
| WO 93/24658 | 12/1993 | (WO) . |
| WO 92/02526 | 2/1994 | (WO) . |
| WO 95/20320 | 8/1995 | (WO) . |
| WO 97/10365 | 3/1997 | (WO) . |
| WO 97/29212 | 8/1997 | (WO) . |
| WO 97/42211 | 11/1997 | (WO) . |
| WO 97/42213 | 11/1997 | (WO) . |
| WO 97/42218 | 11/1997 | (WO) . |
| WO 97/46703 | 12/1997 | (WO) . |
| WO 98/04745 | 2/1998 | (WO) . |
| WO 98/18488 | 5/1998 | (WO) . |

OTHER PUBLICATIONS

Bayer and Wilchek. "Labeling and detection of proteins and glycoproteins." *Nonradioactive Labeling and Detection of Biomolecules.* Kessler, C., Ed. New York: Springer–Verlag, 1992. pp. 91–100.

Cardullo. "Nonradioactive fluorescence energy transfer." *Nonradioactive Labeling and Detection of Biomolecules.* Kessler, C., Ed. New York: Springer–Verlag, 1992. pp. 414–423.

Chee. (Oct. 25, 1996). "Accessing genetic information with high–density DNA arrays," *Science.* 274:610–614.

Cimino et al. (1985). "Psoralens as photactive probes of nucleic acid structure and function: Organic chemistry, photochemistry, and biochemistry," *Ann Rev. Biochem.* 54:1151–1193.

Howard, G. "Labeling proteins with fluorochromes." *Methods in Nonradioactive Detection.* Howard, G., Ed. Norwalk, CT: Appleton and Lange, 1993. pp. 39–68.

Kessler, C. "Overview of nonradioactive labeling systems." *Nonradioactive Labeling and Detection of Biomolecules.* Kessler, C., Ed. New York: Springer–Verlag, 1992. pp. 27–34.

Levenson et al. (1990). "Biotinylated psoralen derivative for labeling nucleic acid hybridization probes," *Methods Enzymol.* 184:577–583.

*Methods in Nonradioactive Detection.* Howard, G. Ed. Norwalk, CT: Appleton and Lange, 1993. pp. 11–27.

*Methods in Nonradioactive Detection.* Howard, G. Ed. Norwalk, CT: Appleton and Lange, 1993. pp. 137–150.

*Nonradioactive Labeling and Detection Systems.* Kessler, C., Ed. New York: Springer–Verlag, 1992. 70–99.

de Saizieu et al. (Jan. 1998). "Bacterial transcript imaging by hybridization of total RNA to oligonucleotide arrays," *Nat. Biotechnol.* 16(1):45–48.

Van de Plas. "Colloidal gold as a marker in molecular biology: The use of ultra–small gold particles." *Nonradioactive Labeling and Detection of Biomolecules.* Kessler, C., Ed. New York: Springer–Verlag, 1992. pp. 116–126.

* cited by examiner

Fig. 1

METHODS AND COMPOSITIONS FOR AMPLIFYING DETECTABLE SIGNALS IN SPECIFIC BINDING ASSAYS

CROSS REFERENCE TO RELATED APPLICATIONS

This application claims the benefit of U.S. Provisional Patent Application Serial No. 60/102,577, filed Sep. 30, 1998, the disclosure of which is incorporated herein by reference in its entirety.

TECHNICAL FIELD

This invention relates generally to methods and compounds for amplifying detectable signals in specific binding assays, particularly nucleic acid hybridization assays.

BACKGROUND ART

Nucleic acid hybridizations are commonly used in biochemical research and diagnostic assays. Generally a single stranded analyte nucleic acid is hybridized to labeled nucleic acid probe, and resulting nucleic acid duplexes are detected. Radioactive and nonradioactive labels have been used. Methods also have been developed to amplify the signal that is detected. For example, large comb-type branched polynucleotides, comprising a first oligonucleotide unit and branches including second oligonucleotide units, have been developed for signal amplification in nucleic acid detection assays. In this application, the branched polynucleotide is hybridized via the first oligonucleotide unit to single stranded analyte nucleic acid and then labeled oligonucleotide is hybridized to the branched polynucleotide via the second oligonucleotide units, as described in U.S. Pat. No. 5,710,264 to Chiron Corporation.

Dendrimers have been developed that are assembled by the sequential hybridization of single DNA strands. Pairwise hybridization of single strands produces monomers with a double stranded center and four single stranded "arms". The monomers can be grown exponentially in sequential hybridization steps, to produce a macromolecule including terminal single stranded arms. The dendrimers may range in size from hundreds to millions of bases. The arms that are not to be hybridized to target can be hybridized to covalently labeled oligonucleotide. These dendrimers are commerically available from Polyprobe, Bala Cynwyd, Pa. Dendrimers for assaying nucleic acids are described in U.S. Pat. Nos. 5,175,270, 5,487,973, and 5,484,904, the disclosures of which are incorporated herein.

Avidin-biotin systems have been developed for use in a variety of detection assays. Methods for the detection and labeling of nucleic acids in biotin systems are described, for example, in "Nonradioactive Labeling and Detection Systems", C. Kessler, Ed., Springer-Verlag, New York, 1992, pp. 70–99; and in "Methods in Nonradioactive Detection,", G. Howard, Ed., Appleton and Lange, Norwalk, Conn. 1993, pp. 11–27 and 137–150.

Methods for the detection of nucleic acid sequences have suffered from drawbacks including background noise, time and labor requirements, lack of specificity and lack of sensitivity. It is an object of the invention to provide materials for the detection of polymers, particularly nucleic acids. It is a particular object of the invention to provide methods and compounds for amplifying labeling signals used in the detection of nucleic acid sequences in specific binding assays. It is a further object of the invention to provide methods and compounds which permit nucleic acid sequences to be detected specifically and rapidly with high sensitivity and high resolution.

DISCLOSURE OF THE INVENTION

Methods and compounds are provided for detecting target molecules using specific binding assays. Methods and compositions are provided that are useful in signal amplification in the detection of the target molecule.

In one embodiment, methods are provided for detecting a nucleic acid target, wherein the method comprises hybridizing a nucleic acid target, comprising a target nucleic acid sequence, to a nucleic acid probe, comprising a probe nucleic acid sequence, wherein the target comprises a binding ligand. The hybridized target is contacted with a receptor comprising multiple sites capable of binding the binding ligand to complex the receptor to the binding ligand, and the receptor is contacted with an amplification reagent, comprising a plurality of the binding ligands, to complex the amplification reagent to the receptor. The presence of the complexed amplification reagent then is detected, for example, by detecting the presence of a detectable label on at least one of the receptor and the amplification reagent.

Optionally, after complexing the amplification reagent to the receptor complexed to the hybridized target, the amplification reagent, comprising a plurality of the binding ligands, is contacted with labeled receptor molecules thereby to complex a plurality of labeled receptor molecules to the amplification reagent, and the labeled receptor molecules complexed to the amplification reagent are detected. This permits the detectable signal to be enhanced and more easily detected.

Labels which may be used include fluorescent labels, gold labels and enzyme labels. Exemplary fluorescent labels include fluorescein, rhodamine, resorufin, or a coumarin. In one preferred embodiment, the binding ligand is biotin and the receptor is avidin or streptavidin.

The amplification reagent may comprise a polymer, such as a poly(amino acid) or a polynucleotide. In one embodiment, the amplification reagent may be an antibody, such as an anti-receptor antibody capable of specifically binding the receptor.

In another embodiment, the amplification molecule may be a DNA matrix. The DNA matrix may include subunits of partially double stranded and partially single stranded DNA molecules. In one embodiment, the DNA matrix molecule includes a plurality of molecules of a first partially double stranded polynucleotide, the polynucleotide having a first molecule end, a second molecule end and a double stranded body portion intermediate of the first and second ends, wherein the first and second ends each comprise at least one of first and second arms consisting of a single strand of polynucleotide, and wherein the single strands are hybridizable with a predetermined nucleic acid sequence of nucleotides in a nucleic acid, and the first and second arms of each of said first and second ends are nonhybridizable with each other. The DNA matrix further includes a plurality of molecules of a second partially double stranded polynucleotide, each polynucleotide including a first molecule end, a second molecule end and a double stranded body portion intermediate the first and second ends, the first and second ends each having at least one of first and second arms consisting of a single strand of polynucleotide that is hybridizable with a predetermined nucleic acid sequence of nucleotides in a nucleic acid, wherein the first and second arms of each of said first and second ends are nonhybridizable with each other. In the DNA matrix, the plurality of molecules of the first polynucleotide and the second polynucleotide are joined together through annealing of one or more arms thereof, to form a matrix, wherein arms of the plurality of first and second polynucleotide molecules located on the outer surface of the matrix are hybridized to nucleic acids having the binding ligand attached thereto.

In one embodiment, the binding ligand is biotin and the receptor is avidin or streptavidin. For example, in the embodiment wherein the amplification reagent is an antibody the biotin may be covalently attached to the antibody. For example, the antibody may be an anti-streptavidin antibody comprising a plurality of biotin molecules covalently attached to the antibody. In an assay, after complexing of the antibody to a streptavidin receptor bound to the biotinylated target nucleic acid, the antibody may be contacted with labeled streptavidin, thereby to complex a plurality of labeled streptavidin molecules to the antibody, and the labeled streptavidin molecules complexed to the antibody then may be detected, thus providing signal amplification in the assay.

In the embodiment wherein the amplification reagent is a DNA matrix comprising single stranded DNA, a binding ligand consisting of biotin may be attached to the DNA matrix by hybridization of a plurality of biotinylated nucleic acids to single strands of the DNA matrix. In this embodiment, after complexing the DNA matrix to the receptor complexed to the hybridized target, the biotinylated DNA matrix is contacted with labeled streptavidin, thereby to complex a plurality of labeled streptavidin molecules to the biotins on the DNA matrix, and the labeled streptavidin molecules complexed to the DNA matrix are detected, thus enhancing the detectable signal.

In one preferred embodiment, the nucleic acid probe is immobilized on a surface. The surface may be, for example, Langmuir Blodgett film, glass, germanium, silicon, (poly) tetrafluorethylene, polystyrene, gallium arsenide, gallium phosphide, silicon oxide, silicon nitride, and combinations thereof.

In one embodiment, the hybridizing of a nucleic acid target, comprising a target nucleic acid sequence, to a nucleic acid probe, comprising a probe nucleic acid sequence is conducted in a hybridization solution comprising a sulfonate buffer.

In a further embodiment, a method for detecting a nucleic acid target is provided, wherein the method includes providing a surface comprising at least 100 nucleic acid probes, each in an area of less than about 0.1 cm$^2$, and each nucleic acid probe having a defined sequence and location on the surface, and contacting the surface with a nucleic acid target, comprising a target nucleic acid sequence, to permit the nucleic acid target to hybridize with at least one selected nucleic acid probe that comprises a probe nucleic acid sequence capable of hybridizing to the target nucleic acid sequence, and wherein the target comprises a binding ligand. The probes are preferably immobilized on the surface, for example by covalent attachment. The method further includes contacting the hydrized target with a receptor comprising multiple sites capable of binding the binding ligand to complex the receptor to the binding ligand; contacting the receptor with an amplification reagent, comprising a plurality of the binding ligands, to complex the amplification reagent to the receptor; and detecting the presence of the complexed amplification reagent. In one embodiment, the amplification reagent comprises an antibody or a DNA matrix, the binding ligand comprises biotin and the receptor comprises streptavidin. In one embodiment, the surface comprising the probes is contacted with the nucleic acid target in a hybridization solution comprising a sulfonate buffer, such as 2-[N-morpholino]ethanesulfonic acid ("MES").

Also provided are complexes including a nucleic acid comprising a binding ligand; a receptor; and an amplification reagent comprising a plurality of the binding ligands. In one embodiment, the binding ligand is biotin and the receptor is streptavidin or avidin.

In another embodiment, there is provided a substrate comprising a surface having immobilized thereon a nucleic acid probe, comprising a probe nucleic acid sequence, hybridized to a nucleic acid target, comprising a target nucleic acid sequence; wherein the target comprises a binding ligand, and wherein the binding ligand on the target is complexed with a receptor comprising multiple sites capable of binding the binding ligand, and wherein the receptor is complexed to an amplification reagent, comprising a plurality of the binding ligands.

MODES FOR CARRYING OUT THE INVENTION

Methods and compounds are provided for detecting target molecules using specific binding assays. In particular, methods are provided for detecting a nucleic acid target.

In one embodiment, the method comprises hybridizing a nucleic acid target, comprising a target nucleic acid sequence, to a nucleic acid probe, comprising a probe nucleic acid sequence, wherein the target comprises a binding ligand. The hybridized target is contacted with a receptor comprising multiple sites capable of binding the binding ligand to complex the receptor to the binding ligand, and the receptor is contacted with an amplification reagent, comprising a plurality of the binding ligands, to complex the amplification reagent to the receptor. The presence of the complexed amplification reagent then is detected, for example, by detecting the presence of a detectable label, such as a fluorescent label, for example, on the receptor or the amplification reagent. Optionally, after complexing the amplification reagent to the receptor complexed to the hybridized target, the amplification reagent, comprising a plurality of the binding ligands, is contacted with labeled receptor molecules thereby to complex a plurality of labeled receptor molecules to the amplification reagent, and the labeled receptor molecules complexed to the amplification reagent are detected. This permits the detectable signal to be enhanced and more easily detected. In one embodiment, the amplification reagent is an antibody or a DNA matrix, the binding ligand is biotin and the receptor is streptavidin.

In another embodiment, an array of different nucleic acid probes immobilized on a surface, each having a defined sequence and location on the surface, may be used in the assays disclosed herein, thus permitting screening and detection of binding of a large number of nucleic acids in a sample.

While nucleic acid targets and probes are discussed in detail herein by way of example, the methods and compounds disclosed herein may be used to detect the binding of other molecules including polypeptides.

Amplification Reagents

The amplification reagent may be any chemical substance that comprises a binding ligand capable of binding to a receptor. Preferably, the amplification molecule includes a plurality of binding ligands capable of binding to a receptor. The ligands may be capable of binding the receptor, for example, via non-covalent specific binding interactions. The amplification reagent may comprise, for example, a polymer, such as a poly(amino acid) or poly(ester).

In one embodiment, the amplification reagent may comprise an antibody. As used herein, the term "antibody" refers to an immunoglobulin molecule or a fragment of an immunoglobulin molecule having the ability to specifically bind to a particular antigen. The antibody may be an anti-receptor antibody specific for the receptor used in the assay. Thus, the antibody may be capable of specifically binding the receptor as the antigen. Antibodies and methods for their manufacture are well known in the art of immunology. The antibody may be produced, for example, by hybridoma cell lines, by immunization to elicit a polyclonal antibody response, or by recombinant host cells that have been transformed with a recombinant DNA expression vector that encodes the antibody. Antibodies include but are not limited to immunoglobulin molecules of any isotype (IgA, IgG, IgE, IgD, IgM), and active fragments including Fab, Fab', F(ab')$_2$, Facb, Fv, ScFv, Fd, V$_H$ and V$_L$. Antibodies include but are not limited to single chain antibodies, chimeric antibodies, mutants, fusion proteins, humanized antibodies and any other modified configuration of an immunoglobulin molecule that comprises an antigen recognition site of the required specificity.

The preparation of antibodies including antibody fragments and other modified forms is described, for example, in "Immunochemistry in Practice," Johnstone and Thorpe, Eds., Blackwell Science, Cambridge, Mass., 1996; "Antibody Engineering," 2$^{nd}$ edition, C. Borrebaeck, Ed., Oxford University Press, New York, 1995; "Immunoassay", E. P. Diamandis and T. K. Christopoulos, Eds., Academic Press, Inc., San Diego, 1996; "Handbook of Experimental Immunology," Herzenberg et al., Eds, Blackwell Science, Cambridge, Mass., 1996; and "Current Protocols in Molecular Biology" F. M. Ausubel et al., Eds., Greene Pub. Associates and Wiley Interscience, 1987, the disclosures of which are incorporated herein. A wide variety of antibodies also are available commercially.

The amplification reagent preferably comprises a plurality of the binding ligands. Preferably, the binding ligands are covalently attached to the amplification reagent. For example, in one embodiment, the binding ligand comprises biotin, the receptor is avidin or streptavidin, and the amplification reagent is an anti-streptavidin antibody. In this embodiment, for example, a plurality of biotin molecules, e.g., about 3–10 biotin molecules, are covalently attached to the antibody.

In one embodiment, the amplification reagent is a polynucleotide matrix. The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. A polynucleotide may comprise modified nucleotides, such as methylated nucleotides and nucleotide analogs. The sequence of nucleotides may be interrupted by non-nucleotide components.

In one embodiment, the amplification reagent is a deoxyribonucleic acid ("DNA") matrix. As used herein, the phrase "DNA matrix" refers to a complex of DNA that comprises one or more deoxyribonucleic acids. The DNA may include purine and pyrimidine bases, or other natural, chemically or biochemically modified, non-natural, or derivatized nucleotide bases. In one embodiment, the DNA matrix is a dendrimer that comprises subunits of partially double stranded and partially single stranded DNA molecules. The dendrimeric DNA matrix includes successive layers of polynucleotides of specific structure, including a double stranded waist and single stranded free arms at the molecule ends, formed by hybridization of the arms to adjacent molecule arms. Exemplary dendrimeric DNA matrices are commercially available from Polyprobe, Bala Cynwyd, Pa., and are described in detail in U.S. Pat. Nos. 5,175,270 and 5,487,973, the disclosures of which are incorporated herein.

For example, to form the dendrimeric DNA matrix, a set of nucleotide strand molecules are provided, e.g., by synthesis on a DNA synthesizer or "gene machine" such as the Model 1500 SYSTEC synthesizer. The molecules may be cloned into specifically modified E. coli vectors for large scale production by known methods. The molecules are hybridized to form DNA matrices.

The dendrimeric DNA matrices include layers of DNA. The outermost layer of the DNA matrix has single stranded sequences at the surface that can hybridize with a predetermined nucleic acid sequence. Each layer is composed of a specific class of matrix monomers. Sequential addition of matrix monomers yields a three dimensional DNA matrix.

One embodiment of the assembly of a DNA dendrimer is provided by reference to FIGS. 1–3 and the description of U.S. Pat. No. 5,175,270. The matrix monomers, for example, are DNA dimers having a middle, double stranded "waist" and four single stranded "arms", as shown in FIG. 2 of U.S. Pat. No. 5,175,270. The matrix monomer and components thereof (i.e., waist and arms) can be of any length. For example, each waist can range from about 25 to about 2500 nucleotides. The single stranded arm can typically range between about 12 and about 1000 nucleotides, and preferably between about 20 and 100 nucleotides in length.

FIG. 1 of U.S. Pat. No. 5,175,270 illustrates seven single stranded DNA oligomers which may be assembled to form the matrix monomer. In each oligomer depicted, the solid lines represent (+) strands while the broken lines represent complementary strand sequences. Each lettered (a–e) segment denotes a unique sequence on the different oligomers. FIG. 2 of U.S. Pat. No. 5,175,270 depicts matrix monomers A, B', B', C' and C' assembled by hybridization of the single stranded DNA oligomer strands numbered 1–7 in FIG. 1 of U.S. Pat. No. 5,175,270. Each matrix monomer thus is a dimer including double stranded (waist) regions and single stranded regions (arms). Sequential addition of matrix monomers A, B', B', C' and C' yields a three dimensional DNA matrix as illustrated in FIG. 3 of U.S. Pat. No. 5,175,270, wherein the three dimensional matrix has a core and a surface layer. Further addition of matrix monomers can be implemented to permit growth of the DNA matrix to include the desired number of layers. Thus, in one embodiment, DNA matrices are assembled by successive hybridization of the matrix monomers as described above using hybridization reaction conditions available in the art, as described in detail in U.S. Pat. No. 5,175,270.

The outermost shell or surface layer will have terminal oligonucleotide arms with a selected sequence. The DNA matrix thus can be conveniently hybridized to a ligand or receptor, or label, that is bound to an oligonucleotide that is the reverse complement to the sequence of the matrix arms.

Thus, in one embodiment, as described in U.S. Pat. No. 5,175,270, the disclosure of which is incorporated herein, the DNA matrix includes a plurality of molecules of a first partially double stranded polynucleotide, the polynucleotide having a first molecule end, a second molecule end and a double stranded body portion intermediate of the first and second ends, wherein the first and second ends each comprise at least one of first and second arms consisting of a single strand of polynucleotide, and wherein the single strands are hybridizable with a predetermined nucleic acid sequence of nucleotides in a nucleic acid, and the first and second arms of each of said first and second ends are nonhybridizable with each other. The DNA matrix further includes a plurality of molecules of a second partially double stranded polynucleotide, each polynucleotide including a first molecule end, a second molecule end and a double stranded body portion intermediate the first and second ends, the first and second ends each having at least one of first and second arms consisting of a single strand of polynucleotide that is hybridizable with a predetermined nucleic acid sequence of nucleotides in a nucleic acid, wherein the first and second arms of each of said first and second ends are non-hybridizable with each other. The plurality of molecules of the first polynucleotide and the second polynucleotide are joined together through annealing of one or more arms thereof, to form a matrix, and at least one non-annealed arm of the plurality of first and second polynucleotide molecules located on the outer surface of the matrix is free to hybridize with a nucleic acid sequence.

Advantageously, the non-annealed arm or arms are hybridizable with a specific nucleic acid sequence of nucleotides in a nucleic acid. Thus, a nucleic acid having a sequence complementary to the specific sequence of the dendrimer may be hybridized to the free arms, using hybridization conditions available in the art, and in one preferred embodiment, may be irreversibly crosslinked using commercially available reagents, such as psoralen. In one embodiment a nucleic acid having a sequence complementary to a specific sequence of the dendrimer arms is covalently attached to a binding ligand, and then a plurality of these nucleic acids are hybridized to the DNA matrix to provide the DNA matrix amplification reagent comprising a plurality of binding ligands.

Amplification Using Antibodies

In one embodiment, a method is provided for detecting hybridization of a nucleic acid target comprising a target sequence to a nucleic acid probe comprising a probe sequence. The nucleic acid probe is preferably immobilized on a surface of a substrate. In one embodiment, a binding ligand is complexed, preferably by covalent attachment, to the nucleic acid target.

In an assay, the immobilized nucleic acid probe is contacted, for example, sequentially, with the nucleic acid target comprising the binding ligand; a receptor comprising multiple sites capable of binding the binding ligand; and an anti-receptor antibody comprising a plurality of the binding ligands that are preferably covalently attached to the antibody. If hybridization of the nucleic acid probe to the target has occurred, then a complex is formed of the binding ligand of the target, the receptor and the antibody. The resulting complex can be detected, e.g., by providing and detecting a detectable label on the receptor or the antibody, or by contacting the complexed antibody with, and detecting, labeled detectable molecules of the receptor that are capable of binding to the binding ligand molecules on the antibody. Detection of the label thus provides a positive indicator of the hybridization of the nucleic acid target and the probe.

In one embodiment, the ligand and receptor are biotin and streptavidin respectively. In this embodiment, there is provided a method of determining the hybridization of a nucleic acid target comprising a target nucleotide sequence with an immobilized nucleic acid probe comprising a probe nucleotide sequence. A biotinylated nucleic acid target is provided. The method comprises: contacting the immobilized nucleic acid probe, for example sequentially, with: the biotinylated nucleic acid target; streptavidin; a biotinylated anti-streptavidin antibody comprising a plurality of biotins; and labeled streptavidin molecules. The streptavidin is labeled with a detectable label, such as a fluorescent label. In this embodiment, the binding by hybridization of the nucleic acid target to the probe may be detected with high sensitivity. Upon hybridization of the probe and the target, the target includes only one biotin moiety to which streptavidin may be complexed. Upon complexation of streptavidin with the biotinylated target, the number of biotin molecules is greatly amplified. Upon complexation of labeled streptavidin to the biotins on the antibody, the number of detectable labels is greatly amplified, thus greatly enhancing the sensitivity of the assay.

Figure 1:
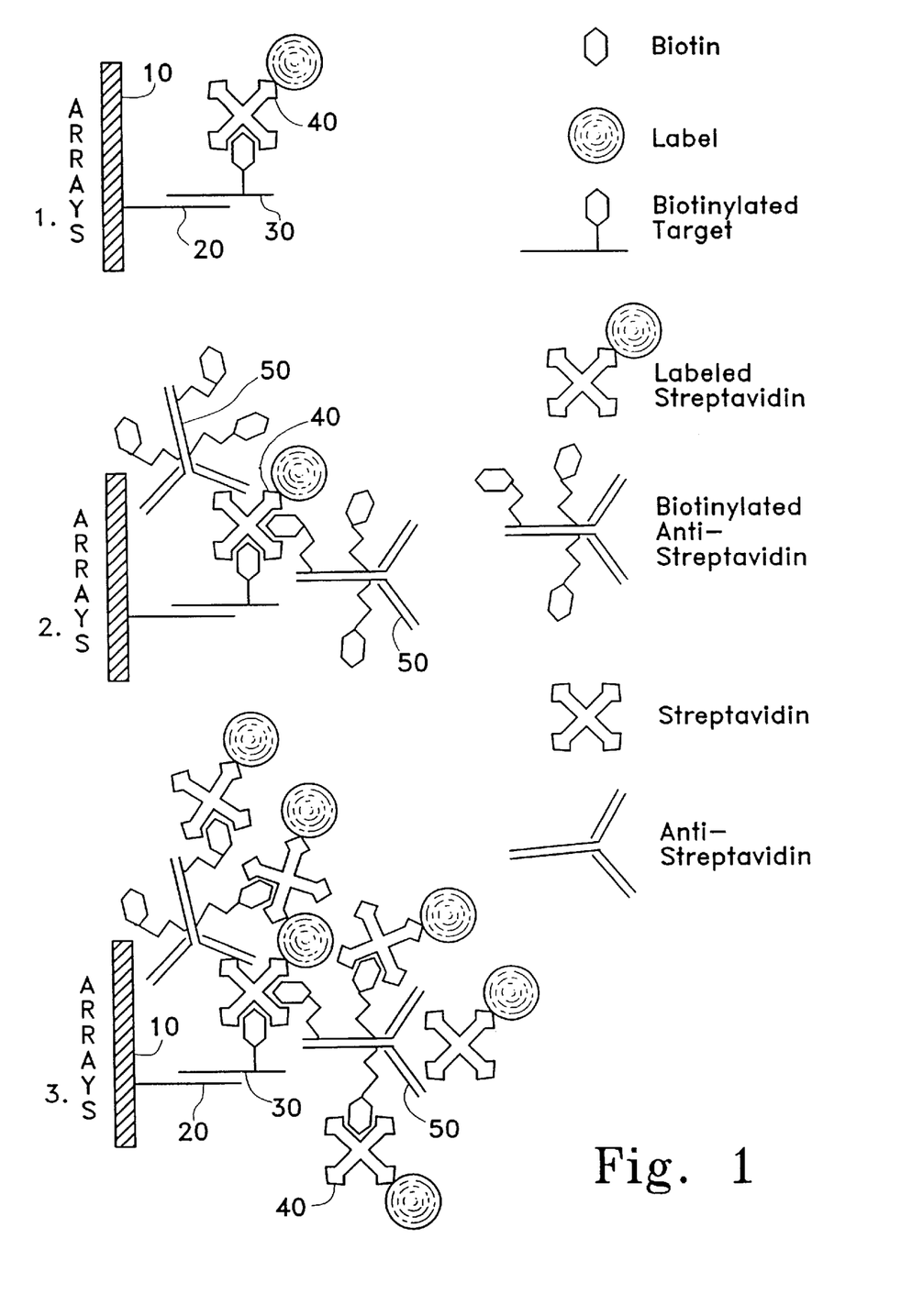
FIG. 1 is a scheme illustrating the detection of a nucleic acid target using an amplification reagent comprising an anti-streptavidin antibody covalently linked to a plurality of biotin molecules.

The assay is illustrated schematically in FIG. 1. FIG. 1, scheme 1, illustrates a nucleic acid probe 20, immobilized on the surface of a solid substrate 10, which is hybridized to a nucleic acid target 30 comprising a covalently attached biotin molecule. The biotin molecule on the target 30 is complexed with a streptavidin molecule which is optionally labeled with a detectable label. The labeled streptavidin 40, as shown in scheme 2 of FIG. 1, is complexed with biotinylated anti-streptavidin antibody 50 which comprises multiple biotin molecules. The antibody thus can interact and complex with the immobilized biotinylated streptavidin via either or both of the antibody binding interaction and the biotin-streptavidin interaction. As shown in scheme 3 of FIG. 1, labeled streptavidin molecules 40 complex with the immobilized antibody 50 and provide multiple labels for detection and signal amplification. The antibody thus provides a bridge to permit multiple labeled streptavidin molecules to be complexed and detected. Additional steps of bridging and signal amplification also may be implemented within the scope of the invention, to enhance the detectable signal of the label.

In one embodiment, the detectable streptavidin which may be used is streptavidin phycoerythrin, which is commercially available, for example, from Molecular Probes (Eugene, Oreg.). Biotinylated anti-streptavidin antibody is available, for example, from Vector Laboratories (Burlingame, Calif.).

Nucleic acid hybridization assay procedures and conditions developed in the art may be used, as described, for example in in: Maniatis et al., "Molecular Cloning: A Laboratory Manual" 2nd Ed., Cold Spring Harbor, N.Y., 1989; Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci.*, U.S.A., 80:1194 (1983).

Nucleic acid hybridization buffers that may be used include phosphate and TRIS buffers, for example, at a pH of about 6 to 8. In one embodiment, a standard saline phosphate ethylenediaminetetraacetic acid ("SSPE") buffer is used. An exemplary phosphate buffer includes: 0.06M $H_2PO_4/HPO_4$, 1M $Na^+$, 0.006M EDTA (ethylenediaminetetraacetic acid), 0.005% Triton®, at a pH of about 6.8, referred to herein as "6×SSPE-T". In one preferred embodiment, in a nucleic acid hybridization assay, a sulfonate hybridization buffer is used, for example a buffer including 2-[N-morpholino] ethanesulfonic acid ("MES"). For example, the hybridization buffer may include about 0.01 M to about 2 M MES or more, e.g., about 0.25 M MES, at a pH, for example, of about 6 to 7. In one embodiment, the MES buffer includes: 0.25M MES, 1M Na$^+$, and 0.005% Tritong® X-100, at a pH of about 5.5–6.7, e.g., 6.7. The hybridization may be conducted, for example, at about 25 to 70° C., for example, about 45° C. Optionally, the buffer may be filtered prior to use, for example, through a 2 μm filter.

Amplification Using DNA Matrices

In one embodiment, a method is provided for detecting binding by hybridization of a nucleic acid target comprising a target sequence to a nucleic acid probe comprising a probe sequence. The nucleic acid probe is preferably immobilized on a surface. In this embodiment, a binding ligand is complexed, preferably by covalent attachment, to the nucleic acid target. The immobilized nucleic acid probe then is contacted, for example sequentially, with the nucleic acid target comprising the binding ligand; a receptor comprising multiple sites capable of binding the binding ligand; and a DNA matrix comprising a plurality of the binding ligands. If hybridization of the nucleic acid probe to the target has occurred, then a complex is formed of the binding ligand of the target, the receptor and the DNA matrix. The resulting complex can be detected, e.g., by providing and detecting a detectable label on the DNA matrix, or by contacting the complexed DNA matrix with, and detecting, labeled detectable molecules of the receptor that are capable of binding to the binding ligand molecules on the DNA matrix. Detection of the label thus provides a positive indicator of the hybridization of the nucleic acid target and the probe.

In one embodiment, the ligand and receptor are biotin and streptavidin respectively. In this embodiment, there is provided a method of determining the hybridization of a nucleic acid target comprising a target nucleotide sequence with an immobilized nucleic acid probe comprising a probe nucleotide sequence. A biotinylated nucleic acid target is provided. The method comprises contacting the immobilized nucleic acid probe, preferably sequentially, with: the biotinylated nucleic acid target; streptavidin; a biotinylated DNA matrix comprising a plurality of biotins; and labeled streptavidin molecules. The streptavidin is labeled with a detectable label, such as a fluorescent label. In this embodiment, the binding by hybridization of the nucleic acid target to the probe may be detected with high sensitivity. After hybridization of the probe and the target, the target includes only one biotin moiety to which streptavidin may be complexed. Streptavidin complexes with the biotinylated target. The biotinylated DNA matrix complexes with the complexed streptavidin. Thus, the number of biotin molecules is greatly amplified. Upon complexation of labeled streptavidin to the biotins on the DNA matrix, the number of detectable labels is greatly amplified, thus greatly enhancing the sensitivity of the assay.

Nucleic acid hybridization assay procedures and conditions developed in the art may be used, as described, for example in in: Maniatis et al., "Molecular Cloning: A Laboratory Manual" 2nd Ed., Cold Spring Harbor, N.Y., 1989; Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci.*, U.S.A., 80:1194 (1983).

Nucleic acid hybridization buffers that may be used include phosphate and TRIS buffers, for example, at a pH of about 6 to 8. In one embodiment, a standard saline phosphate ethylenediaminetetraacetic acid ("SSPE") buffer is used. An exemplary phosphate buffer includes: 0.06M H$_2$PO4/HPO$_4$, 1M Na$^+$, 0.006M EDTA (ethylenediaminetetraacetic acid), 0.005% Triton®, at a pH of about 6.8, referred to herein as "6×SSPE-T". In one preferred embodiment, in a nucleic acid hybridization assay, a sulfonate hybridization buffer is used, for example a buffer including 2-[N-morpholino] ethanesulfonic acid ("MES"). For example, the hybridization buffer may include about 0.01 M to about 2 M MES or more, e.g., about 0.25 M MES, at a pH, for example, of about 6 to 7. In one embodiment, the MES buffer includes: 0.25M MES, 1M Na$^+$, and 0.005% Tritong® X- 100, at a pH of about 6.7. The hybridization may be conducted, for example, at about 25 to 70° C., for example, about 45° C. Optionally, the buffer may be filtered prior to use, for example, through a 2 μm filter.

In one embodiment, in an assay for hybridization of a nucleic acid target to a nucleic acid probe immobilized on a solid surface, such as a biological chip, and the hybridization is conducted at about 45° C. for 16 hrs. This is followed by: a manual wash with 1×ST-T (1M NaCl, 10 mM TRIS-HCl, 0.01% vol/vol Triton X-100, pH 8.0) three times; a wash at a Genechip® Fluidics Station (Affymetrix, Santa Clara, Calif.) using (6×SSPE-T, 22° C., 10×2 (drain 10 cycles, drain and fill twice each cycle)); a wash at 50° C. for 20 min. with 0.1×ST-T (pH 8.0); a stain at 40° C. for 15 min with phycoerythrin ("PE") staining solution such as described in the Examples; a manual wash with 1×ST-T (pH 8.0) three times; a wash with fluidics station wash A (6×SSPE-T, 22° C., 10×2). A scan is taken using an automated confocal fluorescence scanner, the HP GeneArray® 2500 (Affymetrix, Santa Clara, Calif.). Subsequently a solution of Dendrimer with about 10 μl of BSA in ST-T 40° C. is applied for 20 min. This is followed by: a manual wash with 1×ST-T three times; a Fluidics Station wash (6×SSPE-T, 22° C., 10×2); staining at 40° C. for 15 min with 5.0×PE staining solution; a manual wash using 1×ST-T (pH8.0)×3; and a wash at the Fluidics Station (6×SSPE-T, 22° C., 10×2).

Ligand Receptor Pairs

As used herein, the phrase "ligand-receptor pair" refers to a ligand and receptor that are chemical moieties capable of recognizing and binding to each other. The ligand and receptor can be any moieties that are capable of recognizing and binding to each other to form a complex. Additionally, the ligand and receptor may interact via the binding of a third intermediary substance. Typically, the ligand and receptor constituting the ligand-receptor pair are binding molecules that undergo a specific noncovalent binding interaction with each other. The ligand and receptor can be naturally occurring or artificially produced, and optionally may be aggregated with other species.

Examples of ligands and/or receptors include, but are not limited to, agonists and antagonists for cell membrane receptors, toxins and venoms, viral epitopes, hormones such as steroids, hormone receptors, peptides, enzymes and other catalytic polypeptides, enzyme substrates, cofactors, drugs including small organic molecule drugs, opiates, opiate receptors, lectins, sugars, saccharides including polysaccharides, proteins, and antibodies including monoclonal antibodies and synthetic antibody fragments, cells, cell membranes and moieties therein including cell membrane receptors, and organelles. Examples of ligand-receptor pairs include antibody-antigen; lectin-carbohydrate; peptide-cell membrane receptor; protein A-antibody; hapten-antihapten; digoxigenin-anti-digoxigenin; enzyme-cofactor and enzyme-substrate.

Preferably, a ligand-receptor pair includes a receptor that is capable of binding a plurality, e.g., 2, 3, 4 or more, molecules of the ligand. In one preferred embodiment, the ligand-receptor pair is biotin-avidin or biotin-streptavidin. The vitamin biotin is detected by binding of the indicator protein avidin, isolated from egg white, or streptavidin, isolated from *Streptomyces avidinii* bacteria. Avidin and streptavidin have four high affinity binding sites for biotin with a binding constant of about $K=10^{15}$ mol$^{-1}$. Kessler, *Overview of Nonradioactive Labeling Systems* in "Nonradioactive Labeling and Detection of Biomolecules", C. Kessler, Ed., Springer-Verlag, New York, 1992, pp. 27–34, the disclosure of which is incorporated herein.

Amplification reagents used in the assay methods disclosed herein can be attached to any of a variety of members of ligand receptor binding pairs available in the art. In one preferred embodiment, in nucleic acid hydridization assays using an immobilized probe nucleic acid capable of hybridizing to a target nucleic acid, the target nucleic acid is attached to a binding ligand constituting a member of a ligand-receptor binding pair. Additionally, the amplification reagent includes a plurality of the binding ligands. Preferably, the receptor of the ligand receptor pair is capable of binding to two or more molecules of ligand. For example the ligand may be biotin, and the receptor may be avidin or streptavidin, each of which are capable of binding four molecules of biotin. Hybridization of the target nucleic acid to the probe nucleotide is detected by detecting binding of the ligand of the target nucleic acid to the receptor, and binding of the receptor to the binding ligand on the amplification reagent. The amplification reagent is detected, e.g., by providing a label on the amplification reagent, or by complexing the amplification reagent with a plurality of molecules of labeled receptor.

Methods available in the art for attaching binding molecules to nucleic acids may be used to attach ligands or receptors to nucleic acid targets or amplification reagents. In one embodiment, nucleic acids having a binding molecule covalently attached by can be synthesized using a DNA synthesizer and standard phosphoramidite reagents. For example, biotin phosphoramidites for direct labeling of synthetic oligonucleotides may be used. Biotin phosphoramidites are commercially available from Glen Research Corporation, Sterling, Va.

In one embodiment, in the case where the binding ligand is biotin, biotinylated DNA targets can be prepared using nick translation and random primer extension, while biotinylated RNA targets can be synthesized by in vitro transcription using an RNA polymerase. Biotinylated deoxyribonucleoside triphosphates and ribonucleoside triphosphates have been used for the enzymatic preparation of biotinylated DNA and biotinylated RNA. Exemplary methods are disclosed in detail in Rashtchian and Mackey, *Labeling and Detection of Nucleic Acids*, in "Nonradioactive Labeling and Detection of Biomolecules", C. Kessler, Ed., Springer-Verlag, New York, 1992, pp. 70–84. The concentration of biotin molecules may be increased by the use of a psoralen biotin reagent, as described in Levenson et al., *Methods Enzymol.*, 184:577–583 (1990); and Cimono et al., *Ann. Rev. Biochem.* 54:1151–1193 (1985), the disclosures of each of which are incorporated herein. Background hybridization may be reduced by HPLC purification of biotinylated target nucleic acids.

Binding ligands, such as biotins, may be incorporated into dendrimeric DNA matrices, for example, by providing a nucleic acid having a sequence complementary to a specific sequence of the dendrimer arms to which a binding ligand such as biotin is covalently attached, and then hybridizing a plurality of the nucleic acids to the arms of the DNA matrix, thereby to produce a DNA matix amplification reagent comprising a plurality of binding ligands.

Binding ligands, such as biotins, may be attached to amplification molecules, such as polymers, including poly (amino acids), such as antibodies, using methods available in the art. Exemplary methods are disclosed in detail in Bayer and Wilchek, *Labeling and Detection of proteins and Glycoproteins*, in "Nonradioactive Labeling and Detection of Biomolecules", C. Kessler, Ed., Springer-Verlag, New York, 1992, pp. 91–100 and referenced cited therein, the disclosures of which are incorporated herein by reference. Additionally biotinylated antibodies, such as biotinylated anti-streptavidin molecules, are available commercially, for example, from Vector Laboratories (Burlingame, Calif.).

Labels

A variety of labels may be used in the assay methods disclosed herein. The label may be provided on the amplification reagent, the receptor and/or the binding ligand. Examples of labels include fluorescent labels, chemiluminescent labels, and inorganic labels, such as gold, as well as enzymatic labels.

Labels may be used that are detectable, for example, by chromogenic detection, chemiluminescent detection and fluorescent detection. Labels that may be used include marker enzymes such as alkaline phosphatase ("AP"), β-galactosidase or horseradish peroxidase, which are detected using a chromogenic substrate. For example, AP may be detected using 5-bromo-4-chloro-3-indolyl phosphate or nitroblue tetrazolium salt.

Other labels include fluorescent tags such as fluorescein, rhodamine, and resorufin, and derivatives thereof, as well as coumarins such as hydroxycoumarin. Additionally fluorescence resonance energy transfer may be measured, as described in Cardullo, *Nonradiative Fluorescence Resonance Energy Transfer* in "Nonradioactive Labeling and Detection of Biomolecules", C. Kessler, Ed., Springer-Verlag, New York, 1992, pp. 414–423, the disclosure of which is incorporated herein. Optionally inorganic labels may be used, such as colloidal gold particles or ferritin. The use of colloidal gold particles as labels is described, for example, in Van de Plas and Leunissen, *Colloidal Gold as a Marker in Molecular Biology: The Use of Ultra-Small Gold Particles*, in "Nonradioactive Labeling and Detection of Biomolecules", C. Kessler, Ed., Springer-Verlag, New York, 1992, pp. 116–126, the disclosure of which is incorporated herein.

In one preferred embodiment, in an assay to detect a nucleic acid target, using an immobilized probe or array of probes, the binding ligand is biotin and the receptor is avidin or streptavidin, and the amplification reagent is an antibody or a DNA matrix. One or more labels may be conjugated to the avidin or streptavidin and/or the amplification reagent.

Reagents for labeling streptavidin or avidin with a fluorescent tag are commercially available. For example, the reagents, 5(6)-Carboxyfluorescein-N-hydroxysuccinimide ester (FLUOS), 7-amino-4-methyl-coumarin-3-acetic acid-N'-hydroxysuccinimide ester (AMCA, acitvated) and fluorescein isothiocyanate (FITC) are available from Boehringer Mannheim, Indianapolis, Ind. Methods for fluorescently labeling proteins with fluorescent labels, and methods for detection of the fluorescent labels, are described in Howard, G., *Labeling Proteins with Fluorochromes*, in "Methods in Nonradioactive Detection,", G. Howard, Ed., Appleton and Lange, Norwalk, Conn. 1993, pp. 39–68, the disclosure of which is incorporated herein. Additionally, there are a variety of commercially available labeled streptavidin and avidin molecules. Examples include streptavidin-gold, streptavidin-fluorochrome, streptavidin-AMCA, streptavidin-fluorescein, streptavidin-phycoerythrin (STPE), streptavidin-sulforhodamine 101, avidin-FITC and avidin-Texas red®, which are commercially available from Boehringer Mannheim, Indianapolis, Ind.

Assays

The methods and compositions disclosed herein may be used in a variety of applications for assaying for hybridization of a nucleic acid target comprising a target sequence and a nucleic acid probe comprising a probe sequence. In one embodiment, one or more target nucleic acids comprising different target sequences may be screened for hybridization to a high density array of nucleic acid probes comprising different sequences.

As used herein, "hybridization" refers to the binding association between two nucleic acids, for example the non-covalent interaction via base pair hydrogen bonding and base stacking. The ability of two single stranded nucleic acids to hybridize will depend upon factors such as their degree of complementarity as well as the stringency of the hybridization reaction conditions.

As used herein, "stringency" refers to the conditions of a hybridization reaction that influence the degree to which nucleic acids hybridize. Stringent conditions can be selected that allow nucleic acid duplexes to be distinguished based on their degree of mismatch. High stringency is correlated with a lower probability for the formation of a duplex containing mismatched bases. Thus, the higher the stringency, the greater the probability that two single-stranded nucleic acids, capable of forming a mismatched duplex, will remain single-stranded. Conversely, at lower stringency, the probability of formation of a mismatched duplex is increased. The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art. See, for example, Sambrook, et al., "Molecular Cloning: A Laboratory Manual," Second Edition, Cold Spring Harbor Laboratory Press, 1989; Ausubel, et al., "Current Protocols In Molecular Biology," John Wiley & Sons, 1987, 1988, 1989, 1990, 1991, 1992, 1993, 1994, 1995, 1996 and periodic updates; and Hames et al., "Nucleic Acid Hybridization: A Practical Approach," IRL Press, Ltd., 1985. In general, conditions that increase stringency (i.e., select for the formation of more closely-matched duplexes) include higher temperature, lower ionic strength and presence or absence of solvents; lower stringency is favored by lower temperature, higher ionic strength, and lower or higher concentrations of solvents (for example, lower concentrations of formamide or dimethyl sulfoxide). The duration of the hybridization reaction and the concentration of reactants (i.e., single stranded nucleic acid) can also affect stringency, with short reaction times and low reactant concentrations favoring higher stringency.

Methods for conducting nucleic acid hybridization assays have been well developed in the art. Hybridization assay procedures and conditions will vary depending on the application and are selected in accordance with the general binding methods known including those referred to in: Maniatis et al., "Molecular Cloning: A Laboratory Manual" 2nd Ed., Cold Spring Harbor, N.Y., 1989; Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci.*, U.S.A., 80:1194 (1983), each of which are incorporated herein by reference.

Nucleic acid hybridization buffers that may be used include phosphate and TRIS buffers, for example, at a pH of about 6 to 8. In one embodiment, a standard saline phosphate ethylenediaminetetraacetic acid ("SSPE") buffer is used. An exemplary phosphate buffer includes: 0.06M $H_2PO_4/HPO_4$, 1M $Na^+$, 0.006M EDTA (ethylenediaminetetraacetic acid), 0.005% Triton®, at a pH of about 6.8, referred to herein as "6×SSPE-T".

In one embodiment, a method is provided of conducting nucleic acid hybridization assays, wherein the hybridization solution comprises a sulfonate buffer. Sulfonate hybridization buffers include 2-[N-morpholino]ethanesulfonic acid ("MES") and 3-[N-morpholino]propanesulfonic acid ("MOPS"). In one embodiment, the hybridization assay using a sulfonate buffer may be conducted with nucleic acid probes immobilized on a solid surface, such as a silicon or glass surface. The solid surface may be, for example, coated with a silane coating prior to immobilization of the nucleic acid probes. The hybridization assay in a solution comprising a sulfonate buffer may be conducted, for example, at a temperature of about 25 to 70° C., for example, at least about 35° C., or 45° C. or more, and over a time period of, for example, about 10 minutes to 5 hours or more, e.g., about 16 hours or more. The sulfonate buffer may be used, for example in gene expression hybridization assays and polymorphism hybridization assays.

For example, the hybridization buffer may include about 0.01 M to about 2 M MES or more, e.g., about 0.25 M MES, at a pH, for example, of about 6 to 7. In one embodiment, the MES buffer includes: 0.25M MES, 1M $Na^+$, and 0.005% Triton® X-100, at a pH of about 5.5–6.7, e.g. 6.7. The hybridization may be conducted, for example, at about 25 to 70° C., for example, about 45° C. Optionally, the buffer may be filtered prior to use, for example, through a 2 $\mu$m filter. The nucleic acid hybridization buffers may further include surfactants, such as Tween-20 and Triton-X100, as well as additives such as anti-foaming agents.

Methods for screening using arrays of polymers, such as nucleic acids, immobilized on a solid substrate, are disclosed, for example, in U.S. Pat. No. 5,510,270, the disclosure of which is incorporated herein. In this method, an array of diverse nucleic acids is formed on a substrate. The fabrication of arrays of polymers, such as nucleic acids, on a solid substrate, and methods of use of the arrays in different assays, are described in: U.S. Pat. Nos. 5,677,195, 5,624,711, 5,599,695, 5,451,683, 5,424,186, 5,412,087, 5,384,261, 5,252,743 and 5,143,854; PCT WO 92/10092; PCT WO 93/09668; PCT WO 97/10365 and U.S. application Ser. No. 08/388,321, filed Feb. 14, 1995, the disclosures of all of which are incorporated herein. Accessing genetic information using high density DNA arrays is further described in Chee, *Science* 274:610–614 (1996), the disclosure of which is incorporated herein by reference. The combination of photolithographic and fabrication techniques allows each probe sequence to occupy a very small site on the support. The site may be as small as a few microns or even a small molecule. Such probe arrays may be of the type known as Very Large Scale Immobilized Polymer Synthesis (VLSIPS®). U.S. Pat. No. 5,631,734, the disclosure of which is incorporated herein.

Substrates having a surface to which arrays of polynucleotides are attached are referred to herein as "biological chips". The substrate may be, for example, silicon or glass, and can have the thickness of a microscope slide or glass cover slip. Substrates that are transparent to light are useful when the assay involves optical detection, as described, e.g., in U.S. Pat. No. 5,545,531, the disclosure of which is incorporated herein. Other substrates include Langmuir Blodgett film, germanium, (poly)tetrafluorethylene, polystyrene, gallium arsenide, gallium phosphide, silicon oxide, silicon nitride, and combinations thereof.

In the embodiment wherein arrays of nucleic acids are immobilized on a surface, the number of nucleic acid sequences may be selected for different applications, and may be, for example, about 100 or more, or, e.g, in some embodiments, more than $10^5$ or $10^8$. In one embodiment, the surface comprises at least 100 probe nucleic acids each preferably having a different sequence, each probe contained in an area of less than about 0.1 cm$^2$, or, for example, between about 1 $\mu m^2$ and 10,000 $\mu m^2$, and each probe nucleic acid having a defined sequence and location on the surface. In one embodiment, at least 1,000 different nucleic acids are provided on the surface, wherein each nucleic acid is contained within an area less than about $10^{-3}$ cm$^2$, as described, for example, in U.S. Pat. No. 5,510,270.

Arrays of nucleic acids for use in gene expression monitoring are described in PCT WO 97/10365, the disclosure of which is incorporated herein. In one embodiment, arrays of nucleic acid probes are immobilized on a surface, wherein the array comprises more than 100 different nucleic acids and wherein each different nucleic acid is localized in a predetermined area of the surface, and the density of the different oligonucleotides is greater than about 60 different oligonucleotides per 1 cm$^2$.

Arrays of nucleic acids immobilized on a surface which may be used also are described in detail in U.S. Pat. No. 5,744,305, the disclosure of which is incorporated herein. As disclosed therein, on a substrate, nucleic acids with different sequences are immobilized each in a predefined area on a surface. For example, 10, 50, 60, 100, $10^3$, $10^4$, $10^5$, $10^6$, $10^7$, or $10^8$ different monomer sequences may be provided on the substrate. The nucleic acids of a particular sequence are provided within a predefined region of a substrate, having a surface area, for example, of about 1 cm$^2$ to $10^{-10}$ cm$^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, or $10^{-10}$ cm$^2$. For example, in one embodiment, there is provided a planar, non-porous support having at least a first surface, and a plurality of different nucleic acids attached to the first surface at a density exceeding about 400 different nucleic acids/cm$^2$, wherein each of the different nucleic acids is attached to the surface of the solid support in a different predefined region, has a different determinable sequence, and is, for example, at least 4 nucleotides in length. The nucleic acids may be, for example, about 4 to 20 nucleotides in length. The number of different nucleic acids may be, for example, 1000 or more.

In one embodiment, fused silica substrates may be used which have a low glass fluorescence background. Silica substrates permit a low exposure print gap with little or no signal fall off in going from 50 $\mu$m to 20 $\mu$m features, and yields improved performance, including signal and discrimination, for feature sizes less than 50 $\mu$m, for example, 2 $\mu$m. A description of solid phase chemistry, photolithography, and data collecting methods, for the synthesis and use of arrays of materials attached to a solid substrate is provided in U.S. Pat. No. 5,744,305, the disclosure of which is incorporated herein.

In the embodiment where polynucleotides of a known chemical sequence are synthesized at known locations on a substrate, and hybridization of a nucleic acid is detected, and wherein a fluorescent label is detected, detection may be implemented by directing light to relatively small and precisely known locations on the substrate. For example, the substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the substrate and data collection are recorded and managed by an appropriately programmed digital computer, as described in U.S. Pat. No. 5,510,270, the disclosure of which is incorporated herein.

Devices for concurrently processing multiple biological chip assays may be used as described in U.S. Pat. No. 5,545,531, the disclosure of which is incorporated herein. Methods and systems for detecting a labeled marker on a sample on a solid support, wherein the labeled material emits radiation at a wavelength that is different from the excitation wavelength, which radiation is collected by collection optics and imaged onto a detector which generates an image of the sample, are disclosed in U.S. Pat. No. 5,578,832, the disclosure of which is incorporated herein. These methods permit a highly sensitive and resolved image to be obtained at high speed. Methods and apparatus for detection of fluorescently labeled materials are further described in U.S. Pat. Nos. 5,631,734 and 5,324,633, the disclosures of which are incorporated herein.

Applications

The assay methods and compositions described herein may be used in a range of applications including biomedical and genetic research and clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839, the disclosure of which is incorporated herein. The nucleic acid arrays may be used in many other applications including detection of genetic diseases such as cystic fibrosis, diabetes, and acquired diseases such as cancer, as disclosed in U.S. patent application Ser. No. 08/143,312, the disclosure of which is incorporated herein. Genetic mutations may be detected by sequencing by hydridization. In one embodiment, genetic markers may be sequenced and mapped using Type-IIs restriction endonucleases as disclosed in U.S. Pat. No. 5,710,000, the disclosure of which is incorporated herein.

Other applications include chip based genotyping, species identification and phenotypic characterization, as described in U.S. patent application Ser. No. 08/797,812, filed Feb. 7, 1997, and U.S. application Ser. No. 08/629,031, filed Apr. 8, 1996, the disclosures of which are incorporated herein.

Gene expression may be monitored by hybridization of large numbers of mRNAs in parallel using high density arrays of nucleic acids in cells, such as in microorganisms such as yeast, as described in Lockhart et al., *Nature Biotechnology*, 14:1675–1680 (1996), the disclosure of which is incorporated herein. Bacterial transcript imaging by hybridization of total RNA to nucleic acid arrays may be conducted as described in Saizieu et al., *Nature Biotechnology*, 16:45–48 (1998), the disclosure of which is incorporated herein.

In the embodiment wherein solid phase chemistry, photolabile protecting groups and photolithography are used to create light directed spatially addressable parallel chemical synthesis of a large array of polynucleotides on the substrate, as described in U.S. Pat. No. 5,527,681, the disclosure of which is incorporated herein, computer tools may be used for forming arrays. For example, a computer system may be used to select nucleic acid or other polymer probes on the substrate, and design the layout of the array as described in U.S. Pat. No. 5,571,639, the disclosure of which is incorporated herein.

In another embodiment, kits are provided for carrying out amplified nucleic acid hybridization assays that include in packaged combination the materialss: immobilized probe nucleic acids, amplification reagents, and labeled receptors. These reagents will be, for example, in separate containers in the kit. The kit may also include hybridization buffers, wash solutions, negative and positive controls and written instructions for carrying out the assay.

All publications referred to herein are incorporated herein by reference in their entirety.

The invention will be further understood by the following non-limiting examples.

EXAMPLES

Example 1

A nucleic hybridization assay was conducted using a streptavidin-phycoerythrin ("SAPE") and biotinylated anti-streptavidin antibody amplification detection method.

The following materials were used. Solutions were made up in molecular biology grade water (BioWhittaker, Walkersville, Md.).

12×MES Stock Buffer
    0.33M MES Free Acid (Sigma, St. Louis, Mo.)
    0.89 M Na-MES Salt (Sigma)
    Filtered through 0.2 μm filter
    pH 6.5 to 6.8

2×MES Hybridization ("Hyb") Buffer
    2×MES Stock Buffer
    1.77 M NaCl (BioWhittaker, Walkersville, Md.)
    0.04 M EDTA (Sigma, St. Louis, Mo.)
    0.02% Tween 20 (vol/vol) (Pierce, Rockford, Ill.)
    Filtered through 0.2 μm filter.
    pH6.5 to 6.8

0.1×MES Stringent Buffer
    1×MES Stock Buffer 0.03 M NaCl (BioWhittaker, Walkersville, Md.) 0.01% (vol/vol) Tween 20 (Pierce, Rockford, Ill.)
    Filtered through 0.2 μm filter
    pH 6.5 to 6.8

6×SSPE-Tween Buffer
    6×SSPE (0.06M $H_2PO_4$/$HPO_4$, 1M $Na^+$, 0.006M EDTA) (BioWhittaker, Walkersville, Md.)
    0.01% (vol/vol) Tween 20 (Pierce, Rockford, Ill.)
    0.005% (vol/vol) Anti-Foam O-30 (Sigma, St. Louis, Mo.)
    Filter through 0.2 μm filter, add Anti-Foam after filtering
    pH about 7.6

2×Stain Buffer
    2×MES Stock Buffer
    1.85 M NaCl (BioWhittaker, Walkersville, Md.)
    0.10% (vol/vol) Tween 20 (Pierce, Rockford, Ill.)
    0.010% (vol/vol) Anti-Foam O-30 (Sigma, St. Louis, Mo.)
    Filter through 0.2 μm, add Anti-Foam after filtering SAPE Staining Solution
    1×Stain Buffer
    2.0 mg/ml BSA (acetylated) (GibcoBRL, Gaithersburg, Md.)
    10.0 μg/ml SAPE (Molecular Probes, Eugene, Oreg.)
    Stain Volume=500.0 μL Biotinylated Anti-Streptavidin Staining Solution
    1×Stain Buffer
    2.0 mg/ml BSA (acetylated) (GibcoBRL, Gaithersburg, Md.)
    0.1 mg/ml normal goat IgG (Sigma, St. Louis, Mo.)
    3.0 μg/ml biotinylated goat polyclonal anti-streptavidin antibody (Vector
    Laboratories, Burlingame, Calif.)
    Stain Volume=500.0 μL Chip Pre-Treatment Solution
    1×MES Stock Buffer
    0.89 M NaCl (BioWhittaker, Walkersville, Md.)
    0.02 M EDTA (Sigma St. Louis, Mo.)
    0.01% (vol/vol) Tween 20 (Pierce, Rockford, Ill.)

5×Fragmentation Buffer
    200 mM TRIS Acetate pH 8.1
    500 mM potassium acetate
    150 mM Magnesium acetate Sample Preparation (200 μl)
    1×MES Hyb Buffer
    0.5 mg/ml BSA (acetylated) (GibcoBRL, Gaithersburg, Md.)
    0.1 mg/ml herring sperm DNA (Promega Madison, Wis.)
    50 pM biotinylated control oligomer
    10 μg fragmented cRNA sample spike controls (ACTT, Rockville, Md.)—in vitro transcripts (IVTs) of the following plasmids: pglks-BioB; pglks-BioC; pglks-BioD; pglks-Cre; pglbs-lys; pglbs-phe; pglbs-thr; pglbs-trp; pglbs-dap that are fragmented by heat in fragmentation buffer at 95° C. for 35 minutes Assay Protocol A fragmented cRNA sample was prepared as follows. PCR amplification of a plasmid library was conducted followed by in vitro transcription in the presence of biotinylated UTP and CTP to form biotinylated cRNA, which was then fragmented in 1l×Fragmentation Buffer by heating at 95° C. for 35 minutes. See general techniques described in Sambrook, et al., "Molecular Cloning: A Laboratory Manual," Second Edition, Cold Spring Harbor Laboratory Press, 1989; Ausubel, et al., "Current Protocols In Molecular Biology," John Wiley & Sons, 1996; and Lockhart, D. J., et al., *Nature Biotechnology*, 14: 1675–1680 (1996).

200 μL of Chip Pre-Treatment solution was applied to a biological chip having immobilized thereon an array of probe nucleic acids of known sequences. The chip was placed on the rotisserie in the GeneChip Hybridization 320 Oven (Affymetrix, Santa Clara, Calif.) and rotated at 45° C., 60 rpm for 10 minutes.

The sample was heated at 99° C. for 5 minutes and then placed in a 45° C. water bath or heat block for 5 minutes. Chip Pre-Treatment solution was removed from the cartridge and 200 μL of sample at 45° C. was added. The chip was placed on the rotisserie in the GeneChip Hybridization 320 Oven and hybridized at 45° C., 60 rpm for 16 hours.

Sample was removed from the chip and replaced with 200 μL of 6×SSPE-Tween buffer. The chip was subjected to an automated wash/stain protocol on the GeneChip Fluidics Station 400 (Affymetrix, Santa Clara, Calif.) using the EukGE-WS2 fluidics script as follows.

The chip was washed on the fluidics station at 25° C., with 6×SSPE-Tween buffer for 10 cycles with 2 mixes per cycle. This was followed by another wash in 0.1×MES Stringent buffer at 50° C. for 4 cycles with 15 mixes per cycle.

The chip was then stained for 10 minutes at 25° C. on the fluidics station with the SAPE staining solution described above. Staining was followed by a wash with 6×SSPE-Tween buffer at 25° C. for 10 cycles with 4 mixes per cycle.

Example 2

A nucleic hybridization assay was conducted using streptavidin-phycoerythrin and biotinylated anti-streptavidin antibody amplification.

The following materials were used. Buffers were made up in molecular biology grade water (BioWhittaker).

6×SSPE-T Buffer (pH7.6)
- 0.9 M NaCl (BioWhittaker)
- 0.06 $MNaH_2PO_4$ (BioWhittaker)
- 6 mM EDTA(BioWhittaker)
- 0.01% (vol/vol) Triton x-100 (Sigma, St. Louis, Mo.)

1×MES Buffer (pH 6.7)
- 0.1 M MES (MES-hydrate and MES-sodium (Sigma, St. Louis, Mo.)) (made from a stock solution of 12×MES made by combining 6.97 g MES hydrate and 19.39 g MES sodium salt per 100 mL water)
- 1.0 M NaCl (Ambion, Austin, Tex.)
- 0.01% (vol/vol) Triton (Sigma)

0.1×MES Buffer (pH 6.7)
- 0.1 M MES (MES-hydrate and MES-sodium salt (Sigma)
- 0.1 M NaCl (Ambion)
- 0.01% (vol/vol) Triton x-100 (Sigma)

5×SAPE Staining Solution
- 2 μl 1 mg/ml Streptavidin R-Phycoerythrin (Molecular Probes, Eugene, Oreg.)
- 10 μl 50 mg/ml acetylated Bovine Serum Albumin (GibcoBRL Gaithersburg, Md.)
- 188 μl 1×MES buffer Biotinylated Anti-SA Staining Solution
- 1 μg/ml biotinylated goat polyclonal anti-streptavidin antibody ("Anti-SA") Antibody (Vector Laboratories)
- 0.5 mg/ml Acetylated BSA (GibcoBRL)
- in 1×MES buffer Chip Pre-treatment Solution
- 0.5 mg/ml acetylated BSA (GibcoBRL)
- 0.5 mg/ml HS DNA (Promega, Madison, Wis.)
- in 1×MES buffer Sample (200 μl)
- 10 μg fragmented, labeled (biotinylated) cRNA sample
- 0.1 mg/ml HS (herring sperm) DNA (2 μl of 10 mg/ml HS DNA stock, Promega)
- 0.5 mg/ml acetylated BSA (2 μl of 50 mg/ml BSA stock) (GibcoBRL) spike controls (ACTT, Rockville, Md.) (in vitro transcripts (IVTs) of the following plasmids: pglks-BioB; pglks-BioC; pglks-BioD; pglks-Cre; pglbs-lys; pglbs-phe; pglbs-thr; pglbs-trp; pglbs-dap that are fragmented by heat in fragmentation buffer, as described in Example 1, at 95° C. for 35 minutes)
- 1×MES buffer Assay Protocol A fragmented cRNA sample from a murine B-cell library was prepared by PCR amplification of a plasmid library (Clonetech) followed by in vitro transcription in the presence of biotinylated UTP and CTP to form biotinylated cRNA, which was then fragmented in 1×Fragmentation Buffer, as described in Example 1, by heating at 95° C. for 35 minutes. A fragmented cRNA sample also was obtained from human brain cell mRNA (Clonetech). See general techniques described in Sambrook, et al., "Molecular Cloning: A Laboratory Manual," Second Edition, Cold Spring Harbor Laboratory Press, 1989; Ausubel, et al., "Current Protocols In Molecular Biology," John Wiley & Sons, 1996; and Lockhart, D. J., et al., Nature Biotechnology, 14: 1675–1680 (1996).

Hybridization of the murine B-cell cRNA to a biological chip having thereon immobilized nucleic acids with murine B-cell gene sequences, and hybridization of the human brain cell cRNA to a biological chip having thereon immobilized nucleic acids with human brain cell gene sequences, were conducted in the presence of varying levels of added spike controls, and fluorescence was measured before and after antibody amplification of the detectable signal. The biological chips had feature sizes of 24 microns.

In each hybridization assay, 200 μl of chip pretreatment solution was applied to the biological chip. The chip was placed on a rotisserie (Rotamix, Appropriate Technical Resources, Laurel, Md.) at 40° C., at 60 rpm for 15 min. The chip was rinsed in 1×MES buffer.

The sample was heated at 99° C. for 5 min and then put in 45° C. waterbath for less than about 10 minutes before putting it on the chip. 200 μl sample at 45° C. was added to the chip. Hybridization on the rotisserie was conducted at 45° C., at 60 rpm, for 16 or 40 hr.

The chip was washed on a fluidics station (GeneChip Fluidics Station 400, Affymetrix, Santa Clara, Calif.) with 6×SSPE-T at 22° C., 10×2 (10 cycles, drain and fill twice each cycle). The chip was rinsed with 0.1×MES buffer. 200 μl 0.xMES buffer was then applied to wash the chip at 45° C., 60 rpm, for 30 min on the rotisserie. The chip was rinsed with 1×MES buffer.

The chip was stained with 5×SAPE staining solution at 40° C., 60 rpm for 15 min. This was followed by a 6×SSPE-T wash on the fluidics station at 22° C., 10×2.

A first scan was conducted using a HP G2500A GeneArray Scanner (Affymetrix, Santa Clara, Calif.). The 2×multi-image scan was conducted at 570 nm, using a 3 μm pixel size.

The 6×SSPE-T solution was removed from the chip and 200 μl of 1×MES buffer was used to rinse the chip. The chip was stained with 200 μl of anti-SA (anti-streptavidin) staining solution at 40° C., 60 rpm, for 30 min. 200 μl of 1×MES buffer was used to wash the chip manually. This was followed by a 6×SSPE-T wash on the fluidics station at 22° C., 10×2. 1×MES buffer was then used to rinse the chip.

200 μl 5×SAPE stain solution was used to stain the chip at 40° C., 60 rpm for 15 min. The chip was manually washed with 1×MES buffer. This was followed by a 6×SSPE-T wash on the fluidics station at 22° C., 10×2. A second scan was conducted.

The results of the hybridization of the human brain cell cRNA are shown below in Table 1. Table 1 shows in columns 1–13 respectively: 1) concentration of spikes; 2) hybridization time; 3) use or nonuse of antibody; 4) number of genes detected; 5) percent of genes detected; 6) average difference in intensity between matches and mismatches for all signals; 7) average difference in intensity between matches and mismatches for positive signals; 8) background; 9) standard deviation; 10) the value Q corresponding to noise; 11) the value P/Q corresponding to signal/noise ratio; 12) number of spikes detected; 13) percent false negatives or positives.

TABLE 1

| Spikes | Hyb | Ab | # Genes Present | % Genes Present | Avg (all) Avg Diff | Avg (P) Avg Diff | Bkg | sd | Q | P/Q | no. of spikes | % false change |
|---|---|---|---|---|---|---|---|---|---|---|---|---|
| 0 | 40 h | — | 2,564 | 36.2% | 180 | 672 | 703 | 25.2 | 26 | 18.3 | 0 | NA |
| 0 | 40 h | Ab | 3,182 | 45 | 907 | 3,182 | 994 | 39.7 | 37.8 | 51.8 | 0 | NA |
| 0.5 pM | 40 h | — | 3,061 | 43.3 | 339 | 573 | 762 | 32.4 | 28 | 27.2 | 8/12 | 1.31% |
| 0.5 pM | 40 h | Ab | 3,628 | 51.3 | 1,566 | 2,967 | 1,161 | 74.8 | 42 | 70.6 | 12/12 | 2.59% |
| 1.5 pM | 40 h | — | 3,240 | 45.8% | 362 | 544 | 772 | 35.4 | 27.9 | 27.7 | 12/12 | 1.29% |
| 1.5 pM | 40 h | Ab | 3,748 | 53.0% | 1,657 | 3,050 | 1,200 | 79.5 | 43.3 | 70.5 | 12/12 | 3.50% |

The results of the hybridization of the murine B-cell cRNA are shown below in Table 2. Table 2 shows in columns 1–13 respectively: 1) concentration of spikes; 2) hybridization time; 3) use or nonuse of antibody; 4) number of genes detected; 5) percent of genes detected; 6) average difference in intensity between matches and mismatches for all signals; 7) average difference in intensity between matches and mismatches for positive signals; 8) background; 9) standard deviation; 10) the value Q corresponding to noise; 11) the value P/Q corresponding to signal/noise ratio; 12) number of spikes detected; 13) percent false negatives or positives.

TABLE 2

| Spikes | Hyb time | Ab | # Genes Present | % Genes Present | Avg (all) Avg Diff | Avg (P) Avg Diff | Bkgrd | sd | Q | P/Q | no. of spikes | % false change |
|---|---|---|---|---|---|---|---|---|---|---|---|---|
| 0 | 16 h | — | 1,096 | 16.6% | 166 | 969 | 741 | 25.8 | 26.6 | 36.5 | 0 | NA |
| 0 | 40 h | — | 1,240 | 18.8 | 222 | 1,158 | 679 | 24.7 | 25.7 | 45 | 0 | NA |
| 0.15 pM | 16 h | — | 1,162 | 17.6 | 219 | 924 | 723 | 25.8 | 26.3 | 46.4 | 1/22 | 0.77% |
| 0.15 pM | 40 h | — | 1,242 | 18.8 | 210 | 1,148 | 668 | 29.9 | 24.9 | 43.6 | 2/22 | 1.51% |
| 0.5 pM | 16 h | — | 1,110 | 16.8% | 183 | 966 | 741 | 27 | 26.4 | 40.3 | 5/22 | 1.07% |
| 0.5 pM | 40 h | — | 1,309 | 19.8% | 234 | 1,092 | 692 | 27.6 | 25 | 46 | 11/22 | 1.33% |
| 0 | 16 h | +Ab | 1,343 | 20.4% | 626 | 3,002 | 940 | 39.2 | 33.7 | 89.2 | 0 | NA |
| 0 | 40 h | +Ab | 1,375 | 20.8% | 844 | 3,942 | 1,082 | 46.3 | 41.4 | 95.3 | 0 | NA |
| 0.15 pM | 16 h | +Ab | 1,345 | 20.4% | 672 | 3,037 | 955 | 38 | 34.2 | 95.3 | 3/22 | 1.59% |
| 0.15 pM | 40 h | +Ab | 1,431 | 21.7% | 777 | 3,795 | 967 | 44.3 | 35.1 | 99.6 | 2//22 | 2.4% |
| 0.5 pM | 16 h | +Ab | 1,338 | 20.3% | 610 | 3,049 | 944 | 34.2 | 34.3 | 86.3 | 5/22 | 1.33% |
| 0.5 pM | 40 h | +Ab | 1,515 | 23.0% | 862 | 3,563 | 972 | 443 | 34.9 | 104.4 | 16/22 | 1.82% |

What is claimed is:

1. A method for detecting a nucleic acid target, the method comprising:
    a) hybridizing a nucleic acid target, comprising target nucleic acid sequence, to a nucleic acid probe, comprising a probe nucleic acid sequence, wherein the target comprises a binding ligand;
    b) contacting the hybridized target with a receptor comprising multiple sites capable of binding the binding ligand to complex the receptor to the binding ligand,
    c) contacting the receptor with a reagent, comprising a plurality of the binding ligands, to complex the reagent to the receptor; and
    d) detecting the presence of the complexed reagent.

2. The method of claim 1, wherein the reagent comprises an antibody.

3. The method of claim 1, wherein the reagent comprises a DNA matrix.

4. The method of claim 3, wherein the DNA matrix comprises subunits of partially double stranded and partially single stranded DNA molecules.

5. The method of claim 3, wherein the DNA matrix comprises:

a plurality of molecules of a first partially double stranded polynucleotide, the polynucleotide having a first molecule end, a second molecule end and a double stranded body portion intermediate of the first and second ends, wherein the first and second ends each comprise at least one of first and second arms consisting of a single strand of polynucleotide, and wherein the single strands are hybridizable with a predetermined nucleic acid sequence of nucleotides in a nucleic acid, and the first and second arms of each of said first and second ends are nonhybridizable with each other;

a plurality of molecules of a second partially double stranded polynucleotide, each polynucleotide including a first molecule end, a second molecule end and a double stranded body portion intermediate the first and second ends, the first and second ends each having at least one of first and second arms consisting of a single strand of polynucleotide that is hybridizable with a predetermined nucleic acid sequence of nucleotides in a nucleic acid, wherein the first find second arms of each of said first and second ends are non-hybridizable with each other;

wherein the plurality of molecules of the first polynucleotide and the second polynucleotide are joined together during annealing of one or more arm thereof, to form a matrix, and wherein arms of the plurality of first and second polynucleotide molecules located on the outer surface of the matrix are hybridized to nucleic acids having the binding ligand attached thereto.

6. The method of claim 1 wherein at least one of the receptor and the reagent comprises a detectable label; and
wherein step d) comprises detecting the label.

7. The method of claim 1 further comprising labeling at least one of the receptor and the reagent with a detectable label prior to step d); and
wherein step d) comprises detecting the label.

8. The method of claim 1 wherein the method further comprises, after step c), and before step d), the step of contacting the reagent, comprising a plurality of the binding ligands, with labeled receptor molecules thereby to complex a plurality of labeled receptor molecules to the reagent; and
wherein step d) comprises detecting the labeled receptor molecules complexed to the reagent.

9. The method of claim 8, wherein the label is selected from the group consisting of a fluorescent label, a gold label and an enzyme label.

10. The method of claim 9, wherein the fluorescent label is selected from the group consisting of fluorescein, rhodamine, resorufin, and a coumarin.

11. The method of claim 1, wherein the binding ligand comprises biotin and the receptor comprises avidin or streptavidin.

12. The method of claim 1, wherein the reagent comprises an antibody capable of specifically binding the receptor.

13. The method of claim 12, wherein the binding ligand comprises biotin, the receptor comprises avidin or streptavidin, and wherein biotin is covalently attached to the antibody.

14. The method of claim 13, wherein the receptor comprises streptavidin and the antibody is an anti-streptavidin antibody comprising a plurality of biotin molecules covalently attached to the antibody;
wherein the method further comprises, after step c), and before step d), the step of contacting the antibody with labeled streptavidin, thereby to complex a plurality of labeled streptavidin molecules to the antibody; and
wherein step d) comprises detecting the labeled streptavidin molecules complexed to the antibody.

15. The method of claim 11, wherein the reagent comprises a DNA matrix comprising single stranded DNA; and
wherein biotin is attached to the DNA matrix by hybridization of a plurality of biotinylated nucleic acids to single strands of the DNA matrix.

16. The method of claim 15, wherein the method further comprises, after step c), and before step d), the step of contacting the DNA matrix with labeled streptavidin, thereby to complex a plurality of labeled streptavidin molecules to the DNA matrix; and
wherein step d) comprises detecting the labeled streptavidin molecules complexed to the DNA matrix.

17. The method of claim 16, wherein the label is selected from the group consisting of a fluorescent label, a gold label and an enzyme label.

18. The method of claim 17, wherein the fluorescent label is selected from the group consisting of fluorescein, rhodamine, resorufin, and a coumarin.

19. The method of claim 1, wherein the nucleic acid probe is immobilized on a surface.

20. The method of claim 19, wherein the surface is selected from the group consisting of Langmuir Blodgett film, glass, germanium, silicon, (poly)tetrafluorethylene, polystyrene, gallium arsenide, gallium phosphide, silicon oxide, silicon nitride, and combinations thereof.

21. The method of claim 5 wherein, in step (a), the hybridization is conducted in a hybridization solution comprising a sulfonate buffer.

22. The method of claim 14 wherein, in step (a), the hybridization is conducted in a hybridization solution comprising a sulfonate buffer.

23. A method for detecting a nucleic acid target, the method comprising:
a) providing a substrate comprising a surface, the surface comprising at least 100 nucleic acid probes, each nucleic acid probe contained in an area of less than about 0.1 $cm^2$, and each nucleic acid probe having a defined sequence and location on the surface;
b) contacting the surface with a nucleic acid target, comprising a target nucleic acid sequence, to permit the nucleic acid target to hybridize with at least one selected nucleic acid probe that comprises a probe nucleic acid sequence capable of hybridizing to the target nucleic acid sequence, and wherein the target comprises a binding ligand;
c) contacting the hydridized target with a receptor comprising multiple sites capable of binding the binding ligand to complex the receptor to the binding ligand;
d) contacting the receptor with a reagent, comprising a plurality of the binding ligands, to complex the reagent to the receptor; and
e) detecting the presence of the complexed reagent.

24. The method of claim 23 wherein, in step b), the surface is contacted with the nucleic acid target in a hybridization solution comprising a sulfonate buffer.

25. The method of claim 24 wherein the sulfonate buffer is 2-[N-morpholino]ethanesulfonic acid ("MES").

26. The method of claim 23, wherein the reagent comprises a DNA matrix, the binding ligand comprises biotin and the receptor comprises streptavidin.

27. The method of claim 26, wherein the binding ligand comprises biotin, the receptor comprises streptavidin and the reagent comprises an anti-streptavidin antibody.

28. A complex comprising:
a nucleic acid comprising a binding ligand;
a receptor comprising multiple binding sites capable of binding the binding ligand; and
a reagent comprising a plurality of said binding ligands.

29. The complex of claim 28, wherein the binding ligand comprises biotin and the receptor comprises streptavidin or avidin.

30. The complex of claim 29, wherein the reagent comprises a DNA matrix.

31. The complex of claim 29, wherein the reagent comprises an anti-streptavidin antibody.

32. A substrate comprising a surface having immobilized thereon a nucleic acid probe, comprising a probe nucleic acid sequences, hybridized to a nucleic acid target, comprising a target nucleic acid sequence;
wherein the target comprises a binding ligand, and wherein the binding ligand on the target is complexed with a receptor comprising multiple sites capable of binding the binding ligand, and wherein the receptor is complexed to a reagent, comprising a plurality of the binding ligands.

33. The substrate of claim 32, wherein the binding ligand comprises biotin and the receptor comprises streptavidin or avidin.

34. The substrate of claim 33, wherein the reagent comprises a DNA matrix.

35. The substrate of claim 33, wherein the reagent comprises an anti-streptavidin antibody.

* * * * *